US010448969B2

(12) United States Patent
Sutton et al.

(10) Patent No.: US 10,448,969 B2
(45) Date of Patent: Oct. 22, 2019

(54) CLOT REMOVAL DEVICE FOR BLOOD VESSELS

(71) Applicant: Fusion Medical, Inc., Plymouth, MN (US)

(72) Inventors: Gregg Stuart Sutton, Plymouth, MN (US); Eric Joseph Dille, Eden Prairie, MN (US); Jeffery Foster Larson, Dayton, MN (US)

(73) Assignee: Fusion Medical, Inc., Dayton, MN (US)

( * ) Notice: Subject to any disclaimer, the term of this patent is extended or adjusted under 35 U.S.C. 154(b) by 587 days.

(21) Appl. No.: 15/008,253

(22) Filed: Jan. 27, 2016

(65) Prior Publication Data
US 2017/0020556 A1 Jan. 26, 2017

Related U.S. Application Data

(63) Continuation-in-part of application No. 13/890,892, filed on May 9, 2013, now Pat. No. 9,848,881.

(60) Provisional application No. 61/644,796, filed on May 9, 2012.

(51) Int. Cl.
*A61B 17/3207* (2006.01)
*A61B 17/12* (2006.01)
*A61B 17/221* (2006.01)
*A61B 17/22* (2006.01)

(52) U.S. Cl.
CPC ........ *A61B 17/320758* (2013.01); *A61B 17/12109* (2013.01); *A61B 17/221* (2013.01); *A61B 17/320725* (2013.01); *A61B 17/12045* (2013.01); *A61B 2017/22054* (2013.01); *A61B 2017/320775* (2013.01)

(58) Field of Classification Search
CPC ........ A61B 17/3207; A61B 17/320725; A61B 17/320758; A61B 2017/320775
See application file for complete search history.

(56) References Cited

U.S. PATENT DOCUMENTS

| 5,766,191 A | 6/1998 | Trerotola |
| 5,843,103 A | 12/1998 | Wulfman |
| 6,652,548 B2 | 11/2003 | Evans et al. |
| 6,660,014 B2 | 12/2003 | Demarais et al. |
| 6,740,191 B2 | 5/2004 | Mcnamara et al. |
| 6,824,551 B2 | 11/2004 | Trerotola |
| 7,108,704 B2 | 9/2006 | Trerotola |
| 7,524,319 B2 | 4/2009 | Dubrul |
| 8,057,496 B2 | 11/2011 | Fischer, Jr. |
| 2005/0124931 A1 | 6/2005 | Fulton et al. |
| 2008/0051873 A1* | 2/2008 | Cottone ............... A61F 2/91 623/1.16 |
| 2012/0143129 A1 | 6/2012 | Simpson et al. |

(Continued)

OTHER PUBLICATIONS

"File History" for U.S. Appl. No. 13/890,892 downloaded from the USPTO Mar. 10, 2016 (136 pages).

(Continued)

*Primary Examiner* — Ashley L Fishback
(74) *Attorney, Agent, or Firm* — Stoel Rives LLP

(57) ABSTRACT

The invention being disclosed describes a medical device for removal of a thrombus or clot in a vascular setting by using a rotational, expandable basket structure in combination with drug infusion, blood/particle aspiration and clot isolation by distal and proximal occlusion.

31 Claims, 13 Drawing Sheets

(56) References Cited

U.S. PATENT DOCUMENTS

2014/0052103 A1* 2/2014 Cully ............... A61B 17/221
                                                         604/508
2014/0094841 A1   4/2014 Sutton et al.
2014/0371780 A1* 12/2014 Vale ................ A61L 31/022
                                                         606/200

OTHER PUBLICATIONS

Office Action dated Mar. 2, 2017 for U.S. Appl. No. 13/890,892.
Non-Final Office Action or U.S. Appl. No. 13/890,892 dated Mar. 2, 2017 (15 pages).

* cited by examiner

CLOT REMOVAL DEVICE FOR BLOOD VESSELS

CROSS-REFERENCE TO RELATED APPLICATION

This application is a continuation in part application of prior U.S. application Ser. No. 13/890,892, filed May 9, 2013, the contents of which are herein incorporated by reference. Further, this application claims the benefit of U.S. Provisional Application No. 61/644,796, filed May 9, 2012, the contents of which are herein incorporated by reference.

FIELD OF THE TECHNOLOGY

The technology relates to an apparatus and method for removing a clot from a patient's vascular system. Further, the technology optionally relates to a device with an isolation element to isolate the clot while the clot is being removed.

BACKGROUND

The fields of interventional radiology, vascular surgery and cardiology require the removal of clots in the arterial and venous systems to reduce the complications arising from vascular occlusions. Additionally, thrombosis of hemodialysis access grafts/fistulae are common issues that dialysis patient's encounter and must be addressed. Specifically, in the case of deep vein thrombosis (DVT), a disease state in which a patient presents with a blood clot in a peripheral vein, the clot may be removed to resolve the patient's acute symptoms, or to help prevent complications of the DVT, including valve damage, Post Thrombotic Syndrome or embolization/migration of clot to the lung, a potentially fatal condition called pulmonary embolism (pulmonary artery occlusion). These clots are typically removed via surgical, pharmacological, or minimally invasive mechanical or pharmacomechanical means. Techniques used for treatment of the clot include injecting/infusing a thrombolytic agent, tissue plasminogen activator (tPA), into the clot to help dissolve the clot, or alternative methods which involve mechanical removal of the clot using aspiration catheters, rotational baskets or other mechanical maceration devices.

The limitation of these devices include the systemic risks of lytic agent infusion, non-control of mobile clots during removal, inability to adapt to anatomical variations, incomplete thrombus removal by inability to gain wall to wall apposition, bradycardia and hemoglobinuria during rheolysis, hemolysis and vein or arterial wall damage resulting from mechanical removal means. Therefore, a need exists for an improved clot removal device for patients experiencing vascular thrombosis, pulmonary embolism, hemodialysis graft thrombosis and arterial thrombosis.

SUMMARY

In an example embodiment, the technology provides a device for clot removal for vascular thrombosis, the device comprising a main tubular shaft having a distal tip and a control handle coupled to the proximal end of the main tubular shaft. A rotational member is coupled to the main tubular shaft, the rotational member comprising an expandable macerating element configured for degrading and removing blood clots. The macerating element typically includes multiple struts. The struts can be expanded and contracted to allow for various diameters. Typically the macerating element is contracted during insertion into a patient, followed by expansion in the proximity of a blood clot. Contraction and expansion can occur independently of rotation of the macerating element. Thus the macerating element's diameter and rotation are independent of one another.

In some implementations an isolation element is coupled to the main tubular shaft, the isolation element having a first expandable isolation member and a second expandable isolation member. These isolation elements are typically positioned on opposite ends of the macerating element. Thus, typically a rotational member is coupled to the main tubular shaft, the rotational member comprising an expandable macerating element. The rotational member is disposed between the first expandable isolation member and the second expandable isolation member.

In an embodiment, the catheter further comprises an aspiration or infusion port along the main tubular shaft.

In some configurations the first expandable isolation member and the second expandable isolation member are inflatable, either simultaneously or independently of one another first and second expandable isolation members can expand to increase their diameter by varying amounts, depending upon the application. In some embodiments this expansion is at least two times, three times, four times, five times, six times, seven times, eight times, nine times, or ten times. Optionally the expansion is more than ten times. In typical embodiments the expansion is from two to ten times, from two to eight times, or from two to six times. It will be understood, as well, that expansion of the isolation members can stop at intermediate levels. For example, when an isolation element can be expanded from two to six times in diameter, the element can typically be expanded an intermediate amount as well, such as four times. In an embodiment, the first expandable isolation member and the second expandable isolation member comprise an elastic polymer, an inelastic polymer, a metallic compound, or a textile.

The expandable macerating element comprises at least two struts in typical configurations, and generally includes more than two struts. Typical configurations include three, four, five, six, seven, or eight struts. More struts are also used in some confirmations.

In various embodiments, the speed of the rotational member can be nearly infinitely variable between the fastest speed of a motor coupled to the rotational member and a speed of 0 rpms. In an embodiment, the rotational member can rotate at numerous rotational velocities, including (without limitation) ranges of 0 to 100 rpms, 0 to 250 rpms, 0 to 500 rpms, 0 to 1,000 rpms, etc. The variable rotational velocity of the rotational member allows for great flexibility in use, especially in combination with changing of diameter. At some points during a procedure a physician may want a combination of large diameter and high rotational velocity, at other times a large diameter and a low rotational velocity. Similarly, a small diameter and high rotational velocity can be advantageous in some situations, as can a small diameter and low velocity. Such variations in diameter and velocity can depend upon such circumstances as the diameter of the blood vessel, the rigidity of the blood clot, presence of anatomical features (such as venous valves) whether the device is seeking to penetrate the clot (requiring a narrow diameter) or is trying to scour the walls of the blood vessel after most of the clot has been removed (requiring a wider diameter).

In reference now to a specific example construction, the technology provides a catheter for clot removal for vascular thrombosis, comprising: a main tubular shaft comprising a distal tip and a control handle coupled to the proximal end of the main tubular shaft; an isolation element coupled to the main tubular shaft, the isolation element comprising a first expandable isolation member and a second expandable isolation member; a rotational member coupled to the main tubular shaft, the rotational member comprising an expandable macerating element; and an aspiration port disposed along the main tubular shaft between the first expandable isolation member and the second expandable isolation member.

In an embodiment, the technology provides a method for removing a clot, comprising: inserting a catheter into a patient's circulatory system, wherein the catheter comprises a first expandable isolation member, a second expandable isolation member and a rotational member; expanding the first expandable isolation member and the second expandable isolation member; and rotating the rotational member to macerate a clot. Optionally, inn an embodiment, the method can further comprise aspirating the macerated clot from between the first expandable isolation member and the second expandable isolation member. In an embodiment, the method can further comprise collapsing the first expandable isolation member and the second expandable isolation member. In an embodiment, the method can further comprise removing the catheter from the patient's circulatory system.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present application is defined by the appended claims and their legal equivalents.

BRIEF DESCRIPTION OF THE FIGURES

The technology may be more completely understood in connection with the following drawings, in which.

Figure 1:
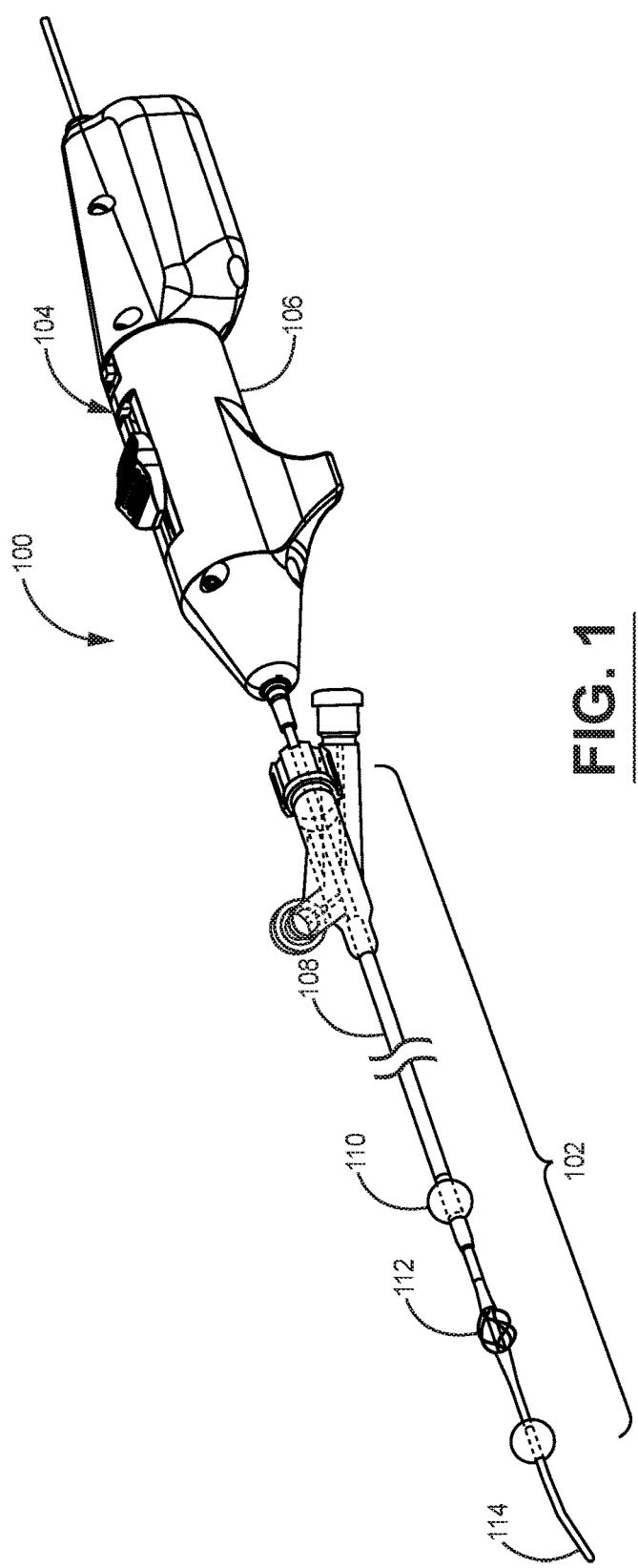
FIG. 1 shows a perspective view of a catheter and control handle, according to an embodiment.

While the technology is susceptible to various modifications and alternative forms, specifics thereof have been shown by way of example and drawings, and will be described in detail. It should be understood, however, that the application is not limited to the particular embodiments described. On the contrary, the application is to cover modifications, equivalents, and alternatives falling within the spirit and scope of the technology.

DETAILED DESCRIPTION

The embodiments of the present technology described herein are not intended to be exhaustive or to limit the technology to the precise forms disclosed in the following detailed description. Rather, the embodiments are chosen and described so that others skilled in the art can appreciate and understand the principles and practices of the present technology.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

It is the purpose of this technology to describe an improved device for removing a clot or other blockage in a patient's circulatory system, such as an artery or vein. The device can be directed toward a medical device for removing thrombus or a clot from the vasculature of a patient. The device of this technology can include a catheter based mechanism with a rotating basket structure in combination with aspiration and/or infusion means as well as distal and proximal clot isolation means. The catheter can be slideable over a guidewire member.

The rotating member can include an expandable macerating element, such as a basket structure. The expandable macerating element can be configured to expand and retract/collapse. The rotating basket structure can include metallic or polymeric struts in a spiral, straight, woven, or patterned configuration. The basket structure can include a plurality of struts, such as to form an expanded elliptical shape or bi-modal elliptical shape. The basket structure can be, for example, expandable in diameter from the catheter diameter (or less) to a much larger diameter, such as 3-24 mm. The diameter of the expandable basket structure can be independently controlled or selected, such as with handle on the proximal end of the device. The diameter expansion control can be independent of the rotational speed of the basket structure. The rotational speed of the basket can be controlled with the proximal handle. The rotational speed of the basket can range from, for example 0-10,000 rpm or 500-10,000 rpm, and can be driven by a DC motor integral to the handle. The basket structure can be made of strut material that provides enough stiffness to macerate and emulsify clots but conformable enough to ride over and not damage venous or arterial structures such as valves.

In an embodiment, the expandable macerating element can include more than one separate and independent basket structures that can be independently expanded or contracted, and independently rotated. For example, the macerating element can include two, three, or four independent basket structures. Optionally more than four basket structures are used, although more than three basket structures can result in a less desirable design due to increases in thickness of the contracted basket and/or complexity of the device.

Yet another embodiment of the technology provides a bi-modal or tri-modal basket shape which optimizes the function of the device when passed through venous or arterial valves. For example, the basket shape can have various shapes and diameters that can be independently controlled. A proximal portion can expand and contract independently of a distal portion, or a medial portion can expand and contract independently of proximal or distal portions The handle can be located on or coupled to the proximal end of the catheter. The handle can include an internal DC motor, gearing/belt system and through lumen access. The catheter can be operated from the handle. The catheter can be configured such that the isolation elements (if present), the rotational member, and the infusion/aspiration element (if present) are able to operate individually, simultaneously, or in combination.

The isolation elements, which are optional in some configurations, can include distal and proximal occlusion elements that generally function by inflation or by mechanical expansion. The occlusive elements may be mounted on an inner guidewire member. The occlusion elements can provide isolation of the clot during maceration and infusion/aspiration so as to inhibit particle embolization and maintenance of lytic concentrations.

In an embodiment, the catheter can further include an infusion/aspiration port or element, such as an outer infusion/aspiration catheter sheath. The infusion/aspiration element can be slideable over the rotational catheter member and can include the proximal occlusion member. The infusion/aspiration element, rotational catheter member, and proximal occlusion member can be controlled with the handle. In some embodiments, the infusion/aspiration element can be controlled without the handle, such as through a valve. The infusion/aspiration element can include a distal to proximal lumen in the outer part of the catheter shaft. The lumen can terminate between the occlusive elements, such as within the isolation zone. The lumen can include an opening optimized for a vacuum. The vacuum can be provided proximally, such as in the handle mechanism, via a vacuum syringe or vacuum pump.

In reference now to the figures, FIG. 1 shows a perspective view of a catheter 100. The catheter 100 can be configured to remove a clot, such as in vascular thrombosis. The catheter 100 can include a distal portion 102 and a proximal portion 104. The distal portion 102 can be at least partially inserted within the patient's circulatory system when the catheter 100 is in use. The proximal portion 104 can include a control handle 106, such as to control the catheter 100 while the catheter 100 is in use.

The catheter 100 can include a main tubular shaft 108, an optional isolation element 110, and a rotational member 112. The main tubular shaft 108 can include a guide wire 114. The catheter 100 can extend over the guide wire 114. The proximal end of the tubular shaft 108 can be coupled to the control handle 106. The isolation element 110 can be coupled to the main tubular shaft 108. The rotational member 112 can be coupled to the main tubular shaft 108. In various embodiments, the rotational member 112 can slide within a portion of the main tubular shaft 108. In various embodiments, the main tubular shaft 108 can include a plurality of tubular shafts, such at least one tubular shaft within another tubular shaft. The plurality of tubular shafts can be concentric.

The isolation element 110 can be configured to isolate an area within the patient's circulatory system. The clot that is being removed can be located within the isolated area between two expandable portions of the isolation element 110.

Figure 2:
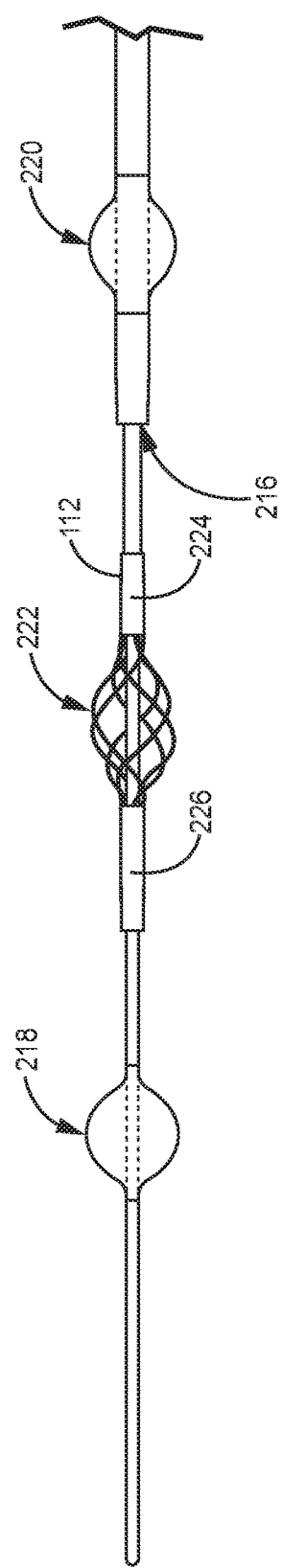
FIG. 2 shows a perspective view of a portion of a catheter, according to an embodiment.

FIG. 2 shows a perspective view of the distal portion 102 of the catheter 100, according to an example embodiment. The catheter 100 includes an aspiration port 216 in the depicted embodiment. In various embodiments, the aspiration port 216 can provide a passage to an inner lumen. In some embodiments, the aspiration port 216 can be located at the end of a shaft, such as shown in FIG. 2, or through an outer wall of a shaft. The aspiration port 216 can be configured to aspirate the area isolated by the isolation elements such as to remove a macerated clot. In some configurations the aspiration port 216 is located along the main tubular shaft 108. The aspiration port 216 can also be located within the area isolated by the isolation element. The aspiration port 216 can be connected to a vacuum pump or syringe, such as to provide suction to the aspiration port 216. It will be understood by those skilled in the art, that the aspiration port 216 can be further configured to be an infusion port, such as to deliver drugs to a treatment site within the patient's vascular system.

Referring again to FIG. 2, in various embodiments, the isolation element can include a first expandable isolation member 218 and a second expandable isolation member 220. Each of the expandable isolation members 218, 220 can be expanded when it is located within the circulatory system of the patient. In an embodiment, the first expandable isolation member can be inserted through the patient's circulatory system and past the clot. The clot can then be located between the first expandable isolation member 218 and the second expandable isolation member 220. The first expandable isolation member 218 and the second expandable isolation member 220 can be expanded to isolate the area between the two isolation members 218, 220. In various embodiments, the aspiration port 216 can be located between the first expandable isolation member 218 and the second expandable isolation member 220. The isolation members 218, 220 can be inflatable, such as to expand the isolation members 218, 220. In an embodiment, the isolation members 218, 220 can include an elastic polymer, an inelastic polymer, a metallic structure, or a textile, or any combination thereof.

The diameter of the isolation members can generally increase at least two times when expanded, such as compared to a collapsed state. In an embodiment, the diameter of the isolation members can increase at least three times when expanded, such as compared to a collapsed state. In an embodiment, the diameter of the isolation members can increase at least four times when expanded, such as compared to a collapsed state. In an embodiment, the diameter of the isolation members can increase at least five times when expanded, such as compared to a collapsed state. In an embodiment, the diameter of the isolation members can increase at least ten times when expanded, such as compared to a collapsed state. In other configurations the diameter of the isolation members can increase at least fifteen times when expanded, such as compared to a collapsed state. In an embodiment, the diameter of the isolation members can increase at least twenty times when expanded, such as compared to a collapsed state. In an embodiment, the diameter of the isolation members can increase at least five times and not more than twenty times when expanded, such as compared to a collapsed state. In an embodiment, the diameter of the isolation members can increase at least six times and not more than twelve times when expanded, such as compared to a collapsed state.

The rotational member 112 can include a macerating element 222. The macerating element 222 can be configured to macerate, cut, shred, or otherwise break up a clot or other blockage. The rotational member 112 can be located within the area isolated by the isolation element, such as between the first isolation member 218 and the second isolation member 220. The macerating element 222 can translate or move between the first isolation member 218 and the second isolation member 220, such as to move closer to or farther from one end of the isolation area, such as to contact a clot. In various embodiments, the macerating element 222 can be collapsible, such as to easily pass through a portion of the patient's circulatory system. In various embodiments, macerating element 222 can be expandable, such as to treat various regions of the circulatory system.

In various embodiments, macerating element can expand to increase its diameter at least two times. In various embodiments, macerating element can expand to increase its diameter at least three times. In various embodiments, macerating element can expand to increase its diameter at least four times. In various embodiments, macerating element can expand to increase its diameter at least five times. In various embodiments, macerating element can expand to increase its diameter at least ten times. In various embodiments, macerating element can expand to increase its diameter at least twelve times. In various embodiments, macerating element can expand to increase its diameter at least fifteen times.

The macerating element 222 can comprise two or more struts, such as extending from a first portion of the rotational member 224 to a second portion of the rotational member 226. In an embodiment, the macerating element 222 can include three or more struts. In an embodiment, the macerating element 222 can include four or more struts. In an embodiment, the macerating element 222 can include five or more struts. In various embodiments, the struts can be flexible, such as to conform to a portion of a patient's circulatory system or transition between a collapsed state and an expanded state.

The rotational member 112 can rotate at speeds of from 0 rpm and up to 10,000 rpm. The rotational member 112 can rotate at speeds of at least 500 rpm and up to 10,000 rpm. In an embodiment, the rotational member 112 can rotate at speeds that range from 1,000 rpm to 5,000 rpm. In an embodiment, the rotational member 112 can rotate at speeds that range from 500 rpm to 2,500 rpm. In various embodiments, a user can select or control the speed of rotation independently of the size of the macerating element. Similarly, a user can select or control the size of the macerating element, such as by collapsing or expanding, independently of the speed of rotation. In various embodiments, a user can select the speed of rotation or the size of the macerating element with the control handle.

Figure 3:
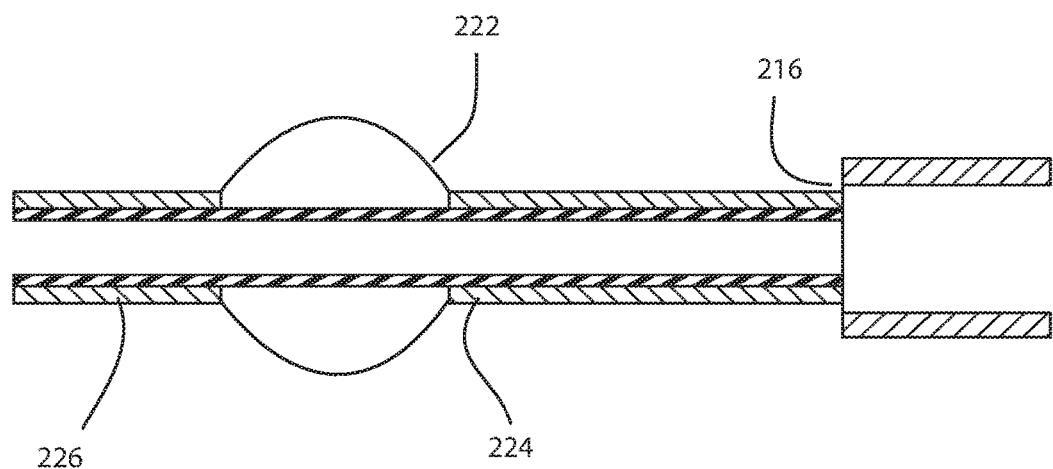
FIG. 3 shows a cross-section view of a portion of a catheter, according to an embodiment.

FIG. 3 shows a cross-sectional view of a portion of the main tubular shaft, according to an embodiment. The main tubular shaft can include multiple tubular shafts, such as the first portion of the rotational member 224 and the second portion of the rotational member 226. The rotational member 112 can include a first portion of the rotational member 224 and a second portion of the rotational member 226. In an embodiment, the second portion 226 can be located distally from the first portion 224. In an embodiment, the second portion 226 can extend through a portion of the first portion 224, such as through an inner lumen defined by the second portion 226. The first portion 224 and the second portion 226 can rotate together, such as at the same speed. The first portion 224 and the second portion 226 can translate with respect to each other, such as the second portion 226 extending further out or away from the aspiration port 216 shown in FIG. 3, such as to collapse the macerating element 222. In an embodiment, the second portion 226 can be moved closer to the first portion 224, such as to expand the macerating element 222.

Figure 4:
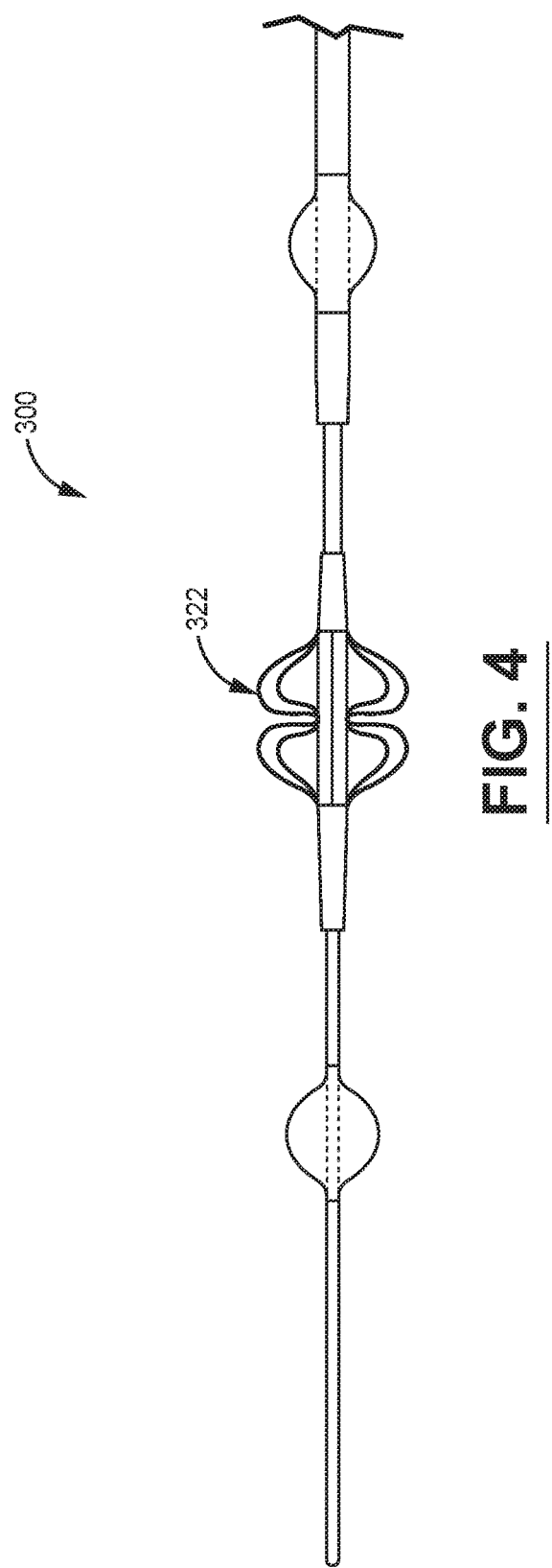
FIG. 4 shows a perspective view of a portion of a catheter, according to an embodiment.

FIG. 4 shows a perspective view of a portion of a catheter 300, according to an embodiment. In an embodiment, the catheter 300 can include a rotational member. The rotational member can include an expandable macerating element 322. The expandable macerating element 322 can be of a bi-modal basket design, such as shown in FIG. 4.

Figure 5:
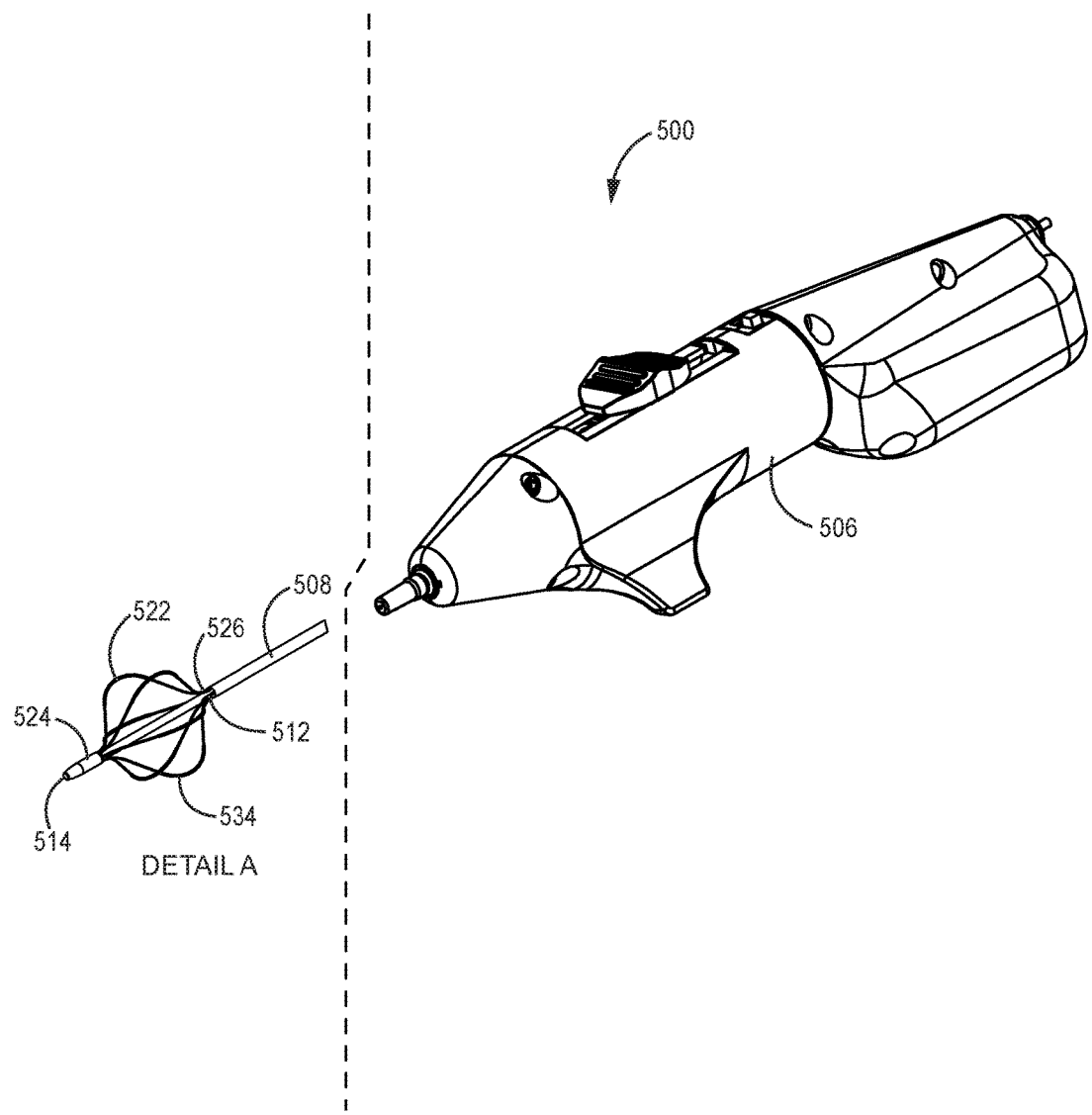
FIG. 5 shows a perspective view of a catheter, according to an embodiment.

FIG. 5 shows a perspective view of a catheter 500, according to an embodiment. The catheter 500 can include a control handle 506, a main tubular shaft 508, a distal tip 514 and a rotational element 512. The rotational element 512 can include a first portion 524 and a second portion 526. The rotational element 512 can include a macerating element 522. In various embodiments, the macerating element 522 can extend from the first portion 524 to the second portion 526. The catheter 500 can be similar to the previously discussed catheters 100, 300. The catheter 500 is shown without an isolation element. It should be understood that the features previously discussed can be included with the features discussed in the following description.

The macerating element 522 can be located along the main tubular shaft 508. The macerating element 522 can be located on the on the distal end of the main tubular shaft 508, such as adjacent to or near the distal tip 514. The macerating element 522 can be expandable and collapsible, such as to change the size of the macerating element 522 in order to facilitate easier entry into the patient's circulatory system and/or exit from the patient's circulatory system and to treat areas of the circulatory of various size. The macerating element 522 can include a plurality of struts 534. The struts 534 can extend from the first portion of the rotational member 524 to the second portion of the rotational member 526. The struts 534 can include a cutting or macerating portion, such that when the cutting or macerating portion comes into contact with a clot, the clot is macerated, broken apart or destroyed. It will be understood, as well, that in certain implementations full length struts extend all the way along the device, from the distal tip back to the control handle, with strut lumens either partially or completely surrounding each strut, typically arranged concentrically around an inner shaft lumen.

Figure 6:
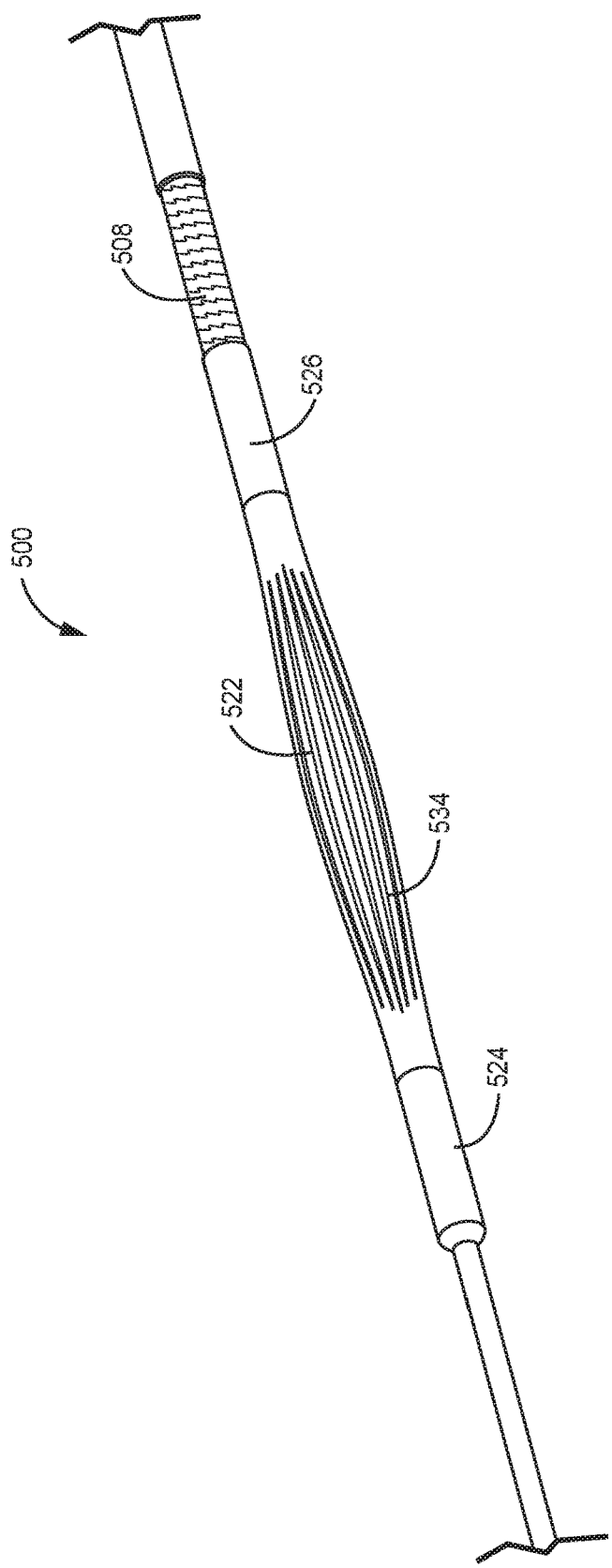
FIG. 6 shows a perspective view of a portion of a catheter, according to an embodiment.

FIG. 6 shows a perspective view of a portion of a catheter 500, according to an embodiment. FIG. 6 shows the macerating element 522 in a collapsed state, such as when the macerating element 522 is entering or exiting the patient's circulatory system. In a collapsed state the first portion of the rotational member 524 can be disposed away from the second portion of the rotational member 526 at a distance approximately equal to the length of a strut. In an embodiment, the macerating element 522 can be substantially cylindrical in a collapsed state. In a collapsed state the struts can be closer to parallel with the main tubular shaft 508 than when the macerating element 522 is in an expanded state. In the collapsed state the struts can lay in a substantially cylindrical arrangement.

Figure 7:
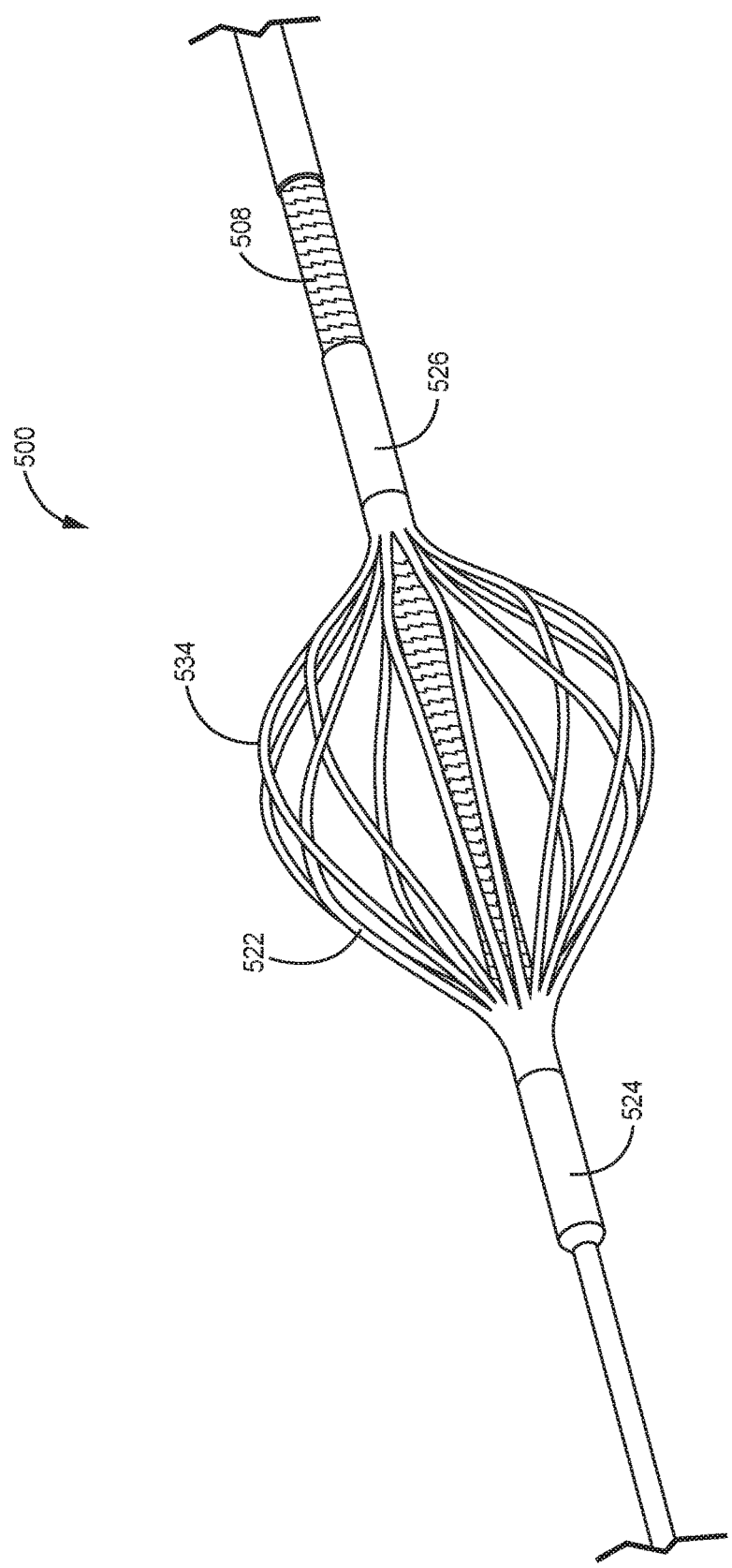
FIG. 7 shows a perspective view of a portion of a catheter, according to an embodiment.

FIG. 7 shows a perspective view of a portion of a catheter 500, according to an embodiment. FIG. 7 shows a view similar to FIG. 6 with the macerating element 522 in an expanded state. The macerating element 522 can be in an expanded state when a portion, such as the middle portion, of the struts 534 are curved or bent radially away from the main tubular shaft 508. In various embodiments, the macerating element 522 can go from a collapsed state to an expanded state by moving or translating the first portion of the rotational member 524 towards the second portion of the rotational member 526 or the second portion of the rotational member 526 towards the first portion of the rotational member 524. Decreasing the distance between the first portion of the rotational member 524 and the second portion of the rotational member 526 can flex a portion of the struts 534 away from the main tubular shaft 508, such as to expand the macerating element 522.

In an embodiment, the distance from the first portion of the rotational member 524 to the second portion of the rotational member 526 can be 10 percent less in an expanded state compared to a collapsed state. the distance from the first portion of the rotational member 524 to the second portion of the rotational member 526 can be 20 percent less in an expanded state compared to a collapsed state. In an embodiment, the distance from the first portion of the rotational member 524 to the second portion of the rotational member 526 can be 25 percent less in an expanded state compared to a collapsed state. In an embodiment, the distance from the first portion of the rotational member 524 to the second portion of the rotational member 526 can be 30% less in an expanded state compared to a collapsed state. In an embodiment, the distance from the first portion of the rotational member 524 to the second portion of the rotational member 526 can be 40 percent less in an expanded state compared to a collapsed state. In an embodiment, the distance from the first portion of the rotational member 524 to the second portion of the rotational member 526 can be 50 percent less in an expanded state compared to a collapsed state. In an embodiment, the distance from the first portion of the rotational member 524 to the second portion of the rotational member 526 can be 60 percent less in an expanded state compared to a collapsed state. In an embodiment, the distance from the first portion of the rotational member 524 to the second portion of the rotational member 526 can be 70 percent less in an expanded state compared to a collapsed state. In an embodiment, the distance from the first portion of the rotational member 524 to the second portion of the rotational member 526 can be 75 percent less in an expanded state compared to a collapsed state. In an embodiment, the distance from the first portion of the rotational member 524 to the second portion of the rotational member 526 can be 80 percent less in an expanded state compared to a collapsed state. In an embodiment, the distance from the first portion of the rotational member 524 to the second portion of the rotational member 526 can be 90 percent less in an expanded state compared to a collapsed state. In an embodiment, the distance from the first portion of the rotational member 524 to the second portion of the rotational member 526 can be 95 percent less in an expanded state compared to a collapsed state.

Figure 8:
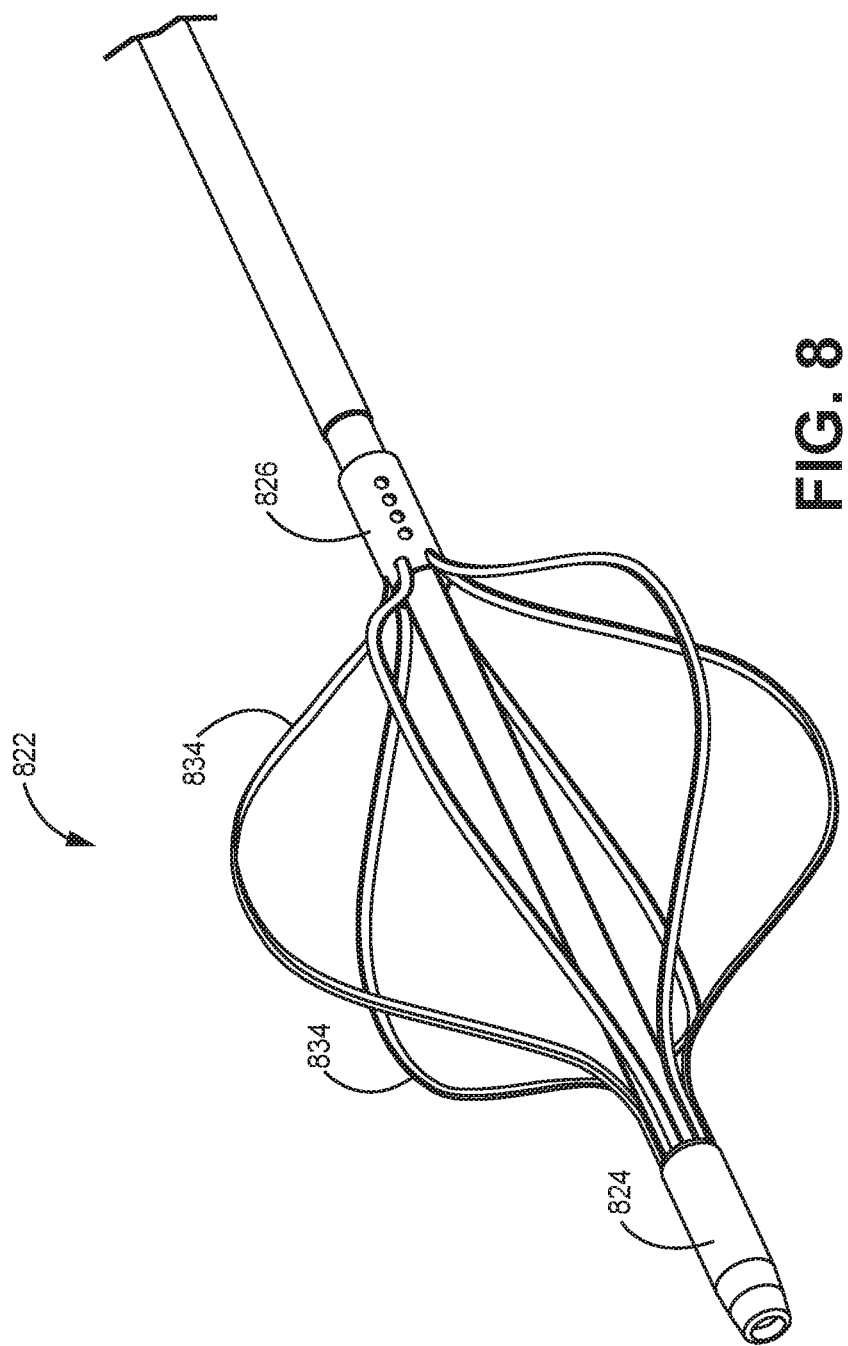
FIG. 8 shows a perspective view of a portion of a catheter, according to an embodiment.

FIG. 8 shows a perspective view of the distal end of a catheter including a macerating element 822. The macerating element 822 can include one or more struts 834. The struts 834 can extend from a first portion of the rotational member 824 to the second portion of the rotational member 826. In various embodiments, each strut 834 can have a substantially identical length. In alternative embodiments, one or more of the struts 834 can have different lengths. In some embodiments, each strut 834 has a length equal to the maximum distance between the first portion of the rotational member 824 and the second portion of the rotational member 826. In some embodiments, the maximum distance between the first portion of the rotational member 824 and the second portion of the rotational member 826 is equal to the length of the shortest strut 834, such as when one or more of the struts 834 have different lengths.

In various embodiments, the struts 834 can be strips or lengths of material that are coupled to the first portion of the rotational member 824 and the second portion of the rotational member 826. In such an embodiment, each strut 834 can be an individual strut, such that each strut 834 is not directly attached to or part of another strut 834.

Figure 9:
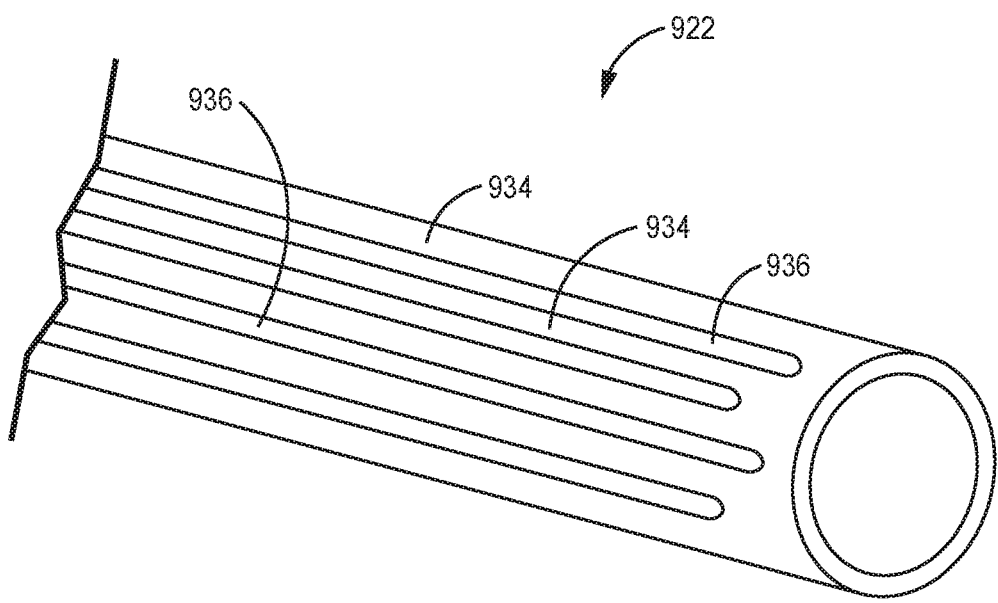
FIG. 9 shows a macerating element, according to an embodiment.

Alternatively, as shown in FIG. 9, in some embodiments the struts 934 can be monolithic, such that all of the struts 934 are from a single piece of material. In some embodiments, the macerating element 922 (shown in a collapsed state in FIG. 9) can define a plurality of voids or open spaces 936, such as an open space 936 between two adjacent struts 934.

In various embodiments, the open spaces 936 can be defined by removing material from the macerating element 922, such as to simultaneously define at least a portion of a strut 934. The material that was previously located in the space that becomes the open space 936 can be cut, excised, burned or otherwise removed from the macerating element 922 to define the open space 936.

In alternative embodiments, the open spaces 936 can be slits or cuts in the macerating element 922. The open spaces 936 can be defined by cutting a slit in the macerating element 922, such as to define a portion of strut 934. In such embodiments, the open spaces 936 can be define by not removing any material from the macerating element 922 or only removing a minimal amount of material, such as the small amount of material that is lost while cutting the material. In such an embodiment, the cut line may not generally define an area.

As shown in FIG. 9, the struts 934 can be staggered or have different lengths. In an embodiment, every other strut 934 is set back or staggered, such as to provide a macerating element 922 in a different shape when it is in an expanded state compared to a macerating element in an expanded shape with the ends of each strut terminating at the same point.

Figure 10:
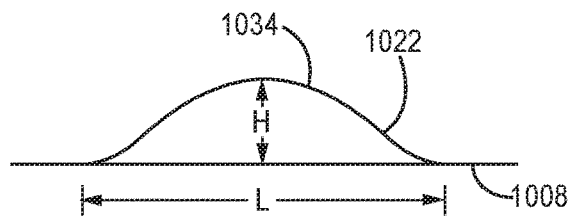
FIG. 10 shows a cross-section of a macerating element, according to an embodiment.

FIGS. 10-16 shows cross-sections of different macerating elements, according to various embodiments. FIGS. 10-16 might only show a portion of the struts included in the macerating element. For example, FIG. 10 shows one strut; however the macerating element in FIG. 10 can include 2, 3, 4, 5, or more struts.

Further, the relationships of struts shown in different macerating elements (FIGS. 10-16) can be used in combination. For example, a macerating element can include struts with a relationship as shown in FIG. 10 and struts with the relationships shown in FIG. 14.

A macerating element can include one or more struts. In an embodiment, a macerating element can include 2 struts. In an embodiment, a macerating element can include 3 struts. In an embodiment, a macerating element can include 4 struts. In an embodiment, a macerating element can include 5 struts. In an embodiment, a macerating element can include 6 struts. In an embodiment, a macerating element can include 7 struts. In an embodiment, a macerating element can include 8 struts. In an embodiment, a macerating element can include 9 struts. In an embodiment, a macerating element can include 10 struts. In an embodiment, a macerating element can include 11 struts. In an embodiment, a macerating element can include 12 struts. In an embodiment, a macerating element can include up to 15 struts. In an embodiment, a macerating element can include up to 20 struts. In an embodiment, a macerating element can include up to 30 struts.

In an embodiment, the struts can be located around the main tubular shaft. In an embodiment, the struts can be equally spaced around the main tubular shaft. For example, when the macerating element includes 8 struts, the struts can be located 45 degrees apart. A macerating element can include struts of different lengths and/or heights.

FIG. 10 shows a cross-section of a macerating element 1022, according to an embodiment. The macerating element 1022 can include a single strut. FIG. 10 can represent a macerating element with a single strut. FIG. 10 can represent a single strut of a macerating element that includes a plurality of struts. In an embodiment, all of the struts in a macerating element are similar, such as they have the same size, shape, and/or position along the length of the main tubular shaft. FIG. 10 represents a macerating element with all of the struts have a similar height, length and position. A strut 1022 can have a height (H) equal to the distance between the peak of the strut to the main tubular shaft 1008. A strut 1022 can have a length (L) equal to the distance between where the strut 1022 separates from the main tubular shaft 1008 to where the strut 1022 returns to the main tubular shaft 1008.

Figure 11:
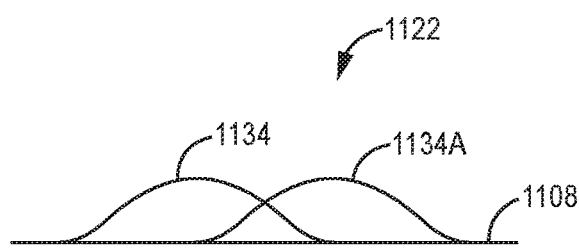
FIG. 11 shows a cross-section of a macerating element, according to an embodiment.

FIG. 11 shows a cross-section of a macerating element 1122, according to an embodiment. The macerating element 1122 can include multiple struts 1134 that have the same height and length. The macerating element 1122 can include multiple struts that have different positions. The position of the strut 1134 can refer to where the strut 1134 is located along the length of the main tubular shaft 1108. As shown in FIG. 11 the first strut 1134 is offset from the second strut 1134A. The first strut 1134 can have the same height and length as the second strut 1134A. In some embodiments, the offset between the struts 1134, 1134A can be achieved by offsetting the struts 1134, 1134A such as shown in FIG. 9.

Figure 12:
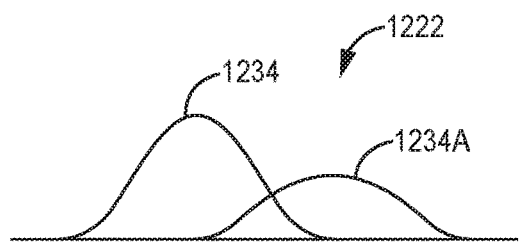
FIG. 12 shows a cross-section of a macerating element, according to an embodiment.

FIG. 12 shows a cross-section of a macerating element 1222, according to an embodiment. The macerating element 1222 can include a first strut 1234 and a second strut 1234A. In an embodiment, the first strut 1234 can be located closer to the distal end of the catheter. In an embodiment, the first strut 1234 can have a larger height than the second strut 1234A. In an embodiment, the first strut 1234 can have the same length as the second strut 1234A. In other embodiments, the first strut 1234 can have a smaller length than the second strut 1234A. In other embodiments, the first strut 1234 can have a larger length than the second strut 1234A.

Figure 13:
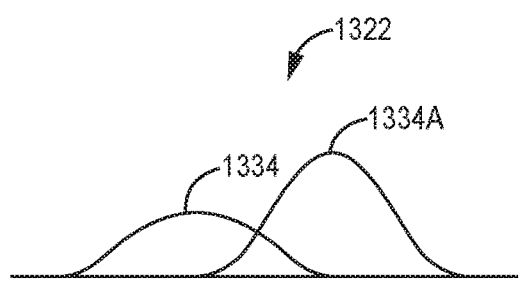
FIG. 13 shows a cross-section of a macerating element, according to an embodiment.

FIG. 13 shows a cross-section of a macerating element 1322, according to an embodiment. The macerating element 1322 can include a first strut 1334 and a second strut 1334A. In an embodiment, the first strut 1334 can be located closer to the distal end of the catheter. In an embodiment, the first strut 1334 can have a smaller height than the second strut 1334A. In an embodiment, the first strut 1334 can have the same length as the second strut 1334A. In other embodiments, the first strut 1334 can have a smaller length than the second strut 1334A. In other embodiments, the first strut 1334 can have a larger length than the second strut 1334A.

Figure 14:
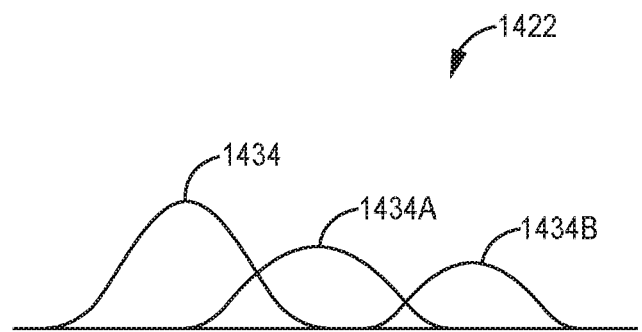
FIG. 14 shows a cross-section of a macerating element, according to an embodiment.
Figure 15:
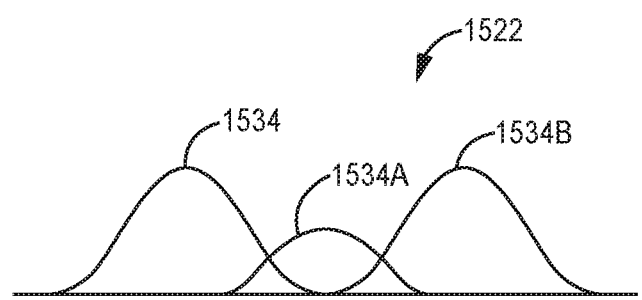
FIG. 15 shows a cross-section of a macerating element, according to an embodiment.
Figure 16:
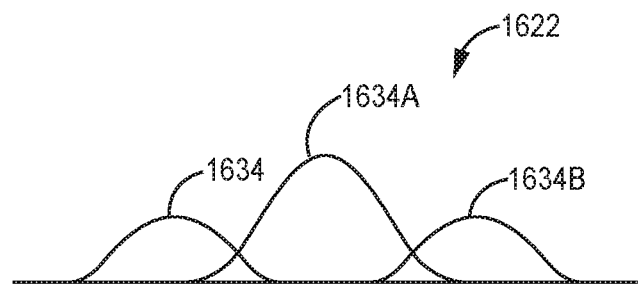
FIG. 16 shows a cross-section of a macerating element, according to an embodiment.

FIG. 14 shows a cross-section of a macerating element 1422, according to an embodiment. The macerating element 1422 can include three struts offset from each other. FIGS. 15 and 16 also show a macerating element with two offsets. In other embodiments, a macerating element can include three offsets, four offsets, five offsets, or more. In some embodiments, all of the struts are offset from each other.

The macerating element 1422 can include a first strut 1434, a second strut 1434A, and a third strut 1434B. In an embodiment, the first strut 1434 can be more distally located than the second strut 1434A and the third strut 1434B. In an embodiment, the first strut 1434 can have a larger height than the second strut 1434A and/or the third strut 1434B. In an embodiment the second strut 1434A can have a larger height than the third strut 1434B. In an embodiment, the second strut 1434a and the third strut 1434B have the same height. In an embodiment (not shown), the third strut 1434B can have height larger than the first strut 1434 and the second strut 1434A, and the second strut 1434A can have a larger height than the first strut 1434.

In an embodiment, the first strut 1434 can have the same length as the second strut 1434A and/or the third strut 1434B. In an embodiment, the first strut 1434 can have the shortest length. In an embodiment, the first strut 1434 can have the longest length. In an embodiment, the first strut 1434 and the second strut 1434A can have the same length, and a different length (either longer or shorter) than the third strut 1434B. In an embodiment, the first strut 1434 and the third strut 1434B can have the same length, and a different length (either longer or shorter) than the second strut 1434A.

FIG. 15 shows a cross-section of a macerating element 1522, according to an embodiment. The macerating element 1522 can include a first strut 1534, a second strut 1534A, and a third strut 1534B. In an embodiment, the first strut 1534 and the third strut 1534B can have the same height. In an embodiment, the first strut 1534 and the third strut 1534B have a larger height than the second strut 1534A FIG. 16 shows a cross-section of a macerating element 1622, according to an embodiment. The macerating element 1622 can include a first strut 1634, a second strut 1634A, and a third strut 1634B. In an embodiment, the first strut 1634 and the third strut 1634B can have the same height. In an embodiment, the first strut 1634 and the third strut 1634B have a smaller height than the second strut 1634A.

Figure 17:
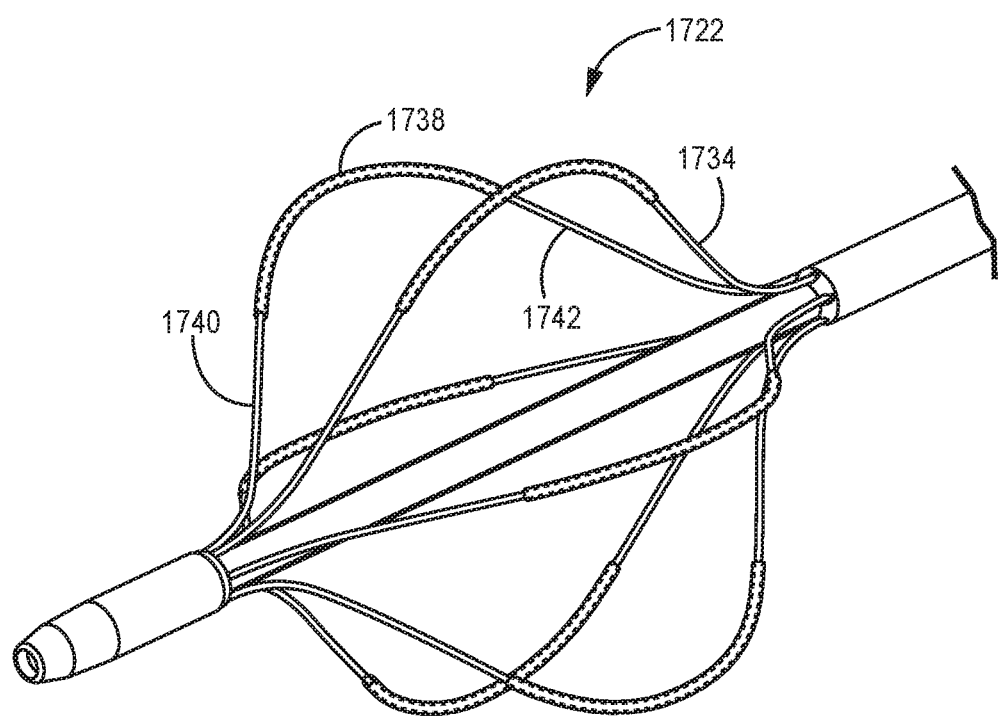
FIG. 17 shows a perspective view of a portion of a catheter, according to an embodiment.

FIG. 17 shows a perspective view of the distal end of a catheter, according to an embodiment. The macerating element 1722 can include a plurality of struts 1734. The struts 1734 can include a coated portion 1738, a first uncoated portion 1740 and a second uncoated portion 1742. In an embodiment, the coated portion 1738 can include a coating over the strut 1734, such as a polymer coating. In various embodiments, the coated portion 1738 can have a smoother surface than the uncoated portions 1740, 1742.

Strut coatings can also include various drug coatings, such as polymer based drug coatings. These include, but are not limited to, poly-L-lactide acid (PLLA) as a carrier for antirestonotic drugs, antiproliferate drugs, immunosuppressive drugs, thrombolytic drugs, fibrolytic drugs, etc. For example, suitable drugs include paclitaxel, tissue plasminogen activator (TPA), streptokinase (SK), and urokinase (UK).

The macerating element 1722 can be configured such that the first uncoated portion 1740 cuts, destroys or macerates a clot that it comes into contact with. The coated portion 1738 can be coated, such as to reduce the surface roughness. The coated portion 1738 can be configured to not cut, damage, or harm the portions of the patient's circulatory system that it contacts.

In an embodiment, the coated portion 1738 contacts the walls of an artery or vein the catheter is located in. The coating can prevent the macerating element 1722 from damaging the walls of the artery or vein. The first uncoated portion 1740 can be configured to macerate or destroy a clot or blockage that it comes into contact with.

An alternative strut design includes recessed pockets or cavities within the struts. These pockets or cavities can include various polymeric and non-polymeric coatings, can function as a drug delivery site, and can also optionally contain abrasive components. The pockets or cavities can be in the form of depressions within the struts, such as a series of intermittent depressions or a smaller number (even one) of longer depressions along a portion or all of the struts. In some implementations the pockets or depressions extend all the way through the strut, and can include protective "buttons", such as made of a polymer, or can include radiopaque markers, abrasive compounds, etc.

Figure 18:
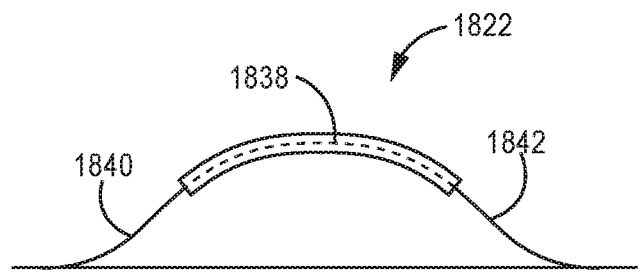
FIG. 18 shows a cross-section of a macerating element, according to an embodiment.

FIG. 18 shows a cross-section of a macerating element 1822, according to an embodiment. In an embodiment, the coated portion 1838 can have a length of at least 25 percent of strut. In an embodiment, the coated portion 1838 can have a length of at least 50 percent of strut. In an embodiment, the coated portion 1838 can have a length of at least 60 percent of strut. In an embodiment, the coated portion 1838 can have a length of at least 70 percent of strut. In an embodiment, the coated portion 1838 can have a length of at least 80 percent of strut. In an embodiment, the entire strut can be coated, such that the coated portion 1838 can have a length of 100 percent of the strut.

Figure 19:
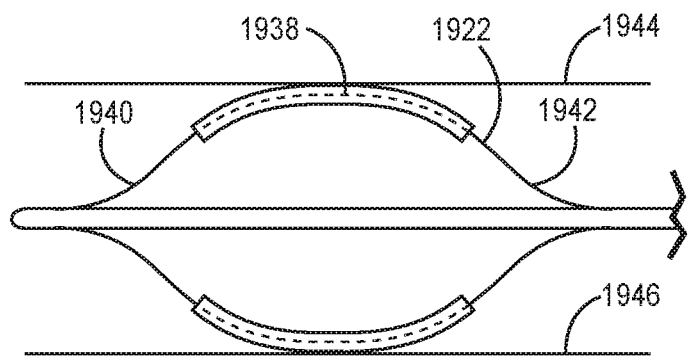
FIG. 19 shows a cross-section of a portion of a catheter in a patient's circulatory system, according to an embodiment.

In an embodiment, the length of the first uncoated portion 1840 and the second uncoated portion 1842 can be equal. In an embodiment, the length of the first uncoated portion 1840 is greater than the length of the second uncoated portion 1842. In an embodiment, the length of the first uncoated portion 1840 is less than the length of the second uncoated portion 1842. FIG. 19 shows a cross-section of a portion of a catheter in a patient's circulatory system, according to an embodiment. Line 1944 and line 1946 can represent walls of an artery or vein within a patient's circulatory system. The macerating element 1922 can be configured such that the coated portions 1938 contact the walls of the vein or artery and the uncoated portions 1940, 1942 do not contact the walls.

Figure 20:
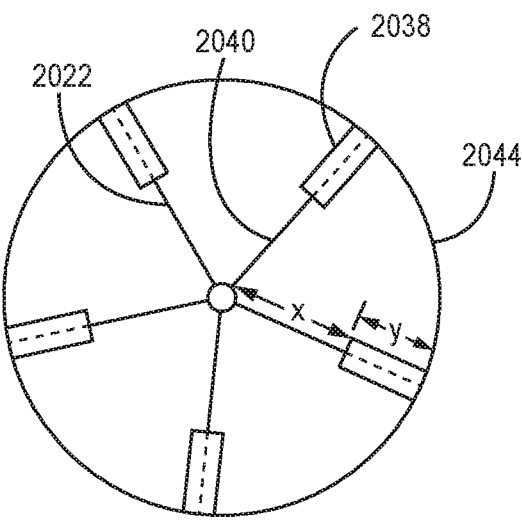
FIG. 20 shows a cross-section of a portion of a catheter in a patient's circulatory system, according to an embodiment.

FIG. 20 shows a cross-section of a portion of a patient's circulatory system with a macerating element 2022 within. FIG. 20 can represent the macerating face of the macerating element 2022. In an embodiment, the length of first uncoated portion (x) can be equal to the length of the coated portion (y). In an embodiment, the length of first uncoated portion can be 10 percent of the length of the coated portion. In an embodiment, the length of first uncoated portion can be 25 percent of the length of the coated portion. In an embodiment, the length of first uncoated portion can be 50 percent of the length of the coated portion. In an embodiment, the length of first uncoated portion can be 75 percent of the length of the coated portion. In an embodiment, the length of first uncoated portion can be 90 percent of the length of the coated portion. In an embodiment, the length of the uncoated portion can be 0 percent, such that the entire strut is coated.

In an embodiment, the length of coated portion can be 10 percent of the length of the uncoated portion. In an embodiment, the length of coated portion can be 25 percent of the length of the uncoated portion. In an embodiment, the length of coated portion can be 50 percent of the length of the uncoated portion. In an embodiment, the length of coated portion can be 75 percent of the length of the uncoated portion. In an embodiment, the length of coated portion can be 90 percent of the length of the uncoated portion.

In an embodiment, a strut can include an abrasive side and a non-abrasive side. The abrasive can be aggressive or non-aggressive. The strut can be configured such that when the macerating element is rotating in a first direction the abrasive side is the leading side of the strut and when the macerating element is rotating in a second direction the non-abrasive side is the leading side of the strut. In some embodiments, the abrasive side can have a coating, such as an abrasive polymer. In some embodiments, the abrasive side can have a profile such as a saw tooth edge. In some embodiments, the aggressive side can have both a profile and an abrasive coating.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this technology pertains. All publications and patent applications are herein incorporated by reference to the same extent as if each individual publication or patent application was specifically and individually indicated by reference.

The technology has been described with reference to various specific and preferred embodiments and techniques. However, it should be understood that many variations and modifications may be made while remaining within the spirit and scope of the technology.

We claim:

1. A catheter for blockage removal for a circulatory system, comprising:
a main tubular shaft comprising a distal tip and a control handle coupled to a proximal end of the main tubular shaft; and
a rotational member coupled to the main tubular shaft, the rotational member comprising an expandable macerating element;
wherein the expandable macerating element comprises a plurality of struts that each include a first portion, a second portion, and a third portion, the first portion is distal to the second and third portions, the second portion is distal to the third portion and proximal to the first portion, and the third portion is proximal to the first and second portions,
wherein the first and third portions comprise an abrasive material and the second portion is smooth, and
wherein the diameter and speed of the rotational member can be independently adjusted during removal of a blockage in the circulatory system.

2. The catheter of claim 1, wherein the smooth portion comprises a low-friction coating.

3. The catheter of claim 1, wherein the abrasive material is along a leading edge of the macerating element.

4. The catheter of claim 1, wherein the abrasive material comprises an abrasive polymer.

5. The catheter according to claim 1, further comprising an aspiration port along the main tubular shaft.

6. The catheter according to claim 5, wherein the aspiration port is located between a first expandable isolation member and the second expandable isolation member.

7. The catheter according to claim 6, wherein the first expandable isolation member and the second expandable isolation member are inflatable.

8. The catheter according to claim 6, wherein the first and second expandable isolation members can expand to increase their volume by at least five times.

9. The catheter according to claim 6, wherein the first expandable isolation member and the second expandable isolation member comprise an elastic polymer.

10. The catheter according to claim 1, wherein the expandable macerating element comprises at least two struts.

11. The catheter according to claim 1, wherein the rotational member can rotate at varying rotational velocities.

12. The catheter according to claim 1, wherein the rotational member can rotate at least 500 rpms.

13. A catheter for blockage removal for a circulatory system, comprising:
a main tubular shaft comprising a distal tip and a control handle coupled to a proximal end of the main tubular shaft; and
a rotational member coupled to the main tubular shaft, the rotational member comprising an expandable macerating element with a plurality of struts, the expandable macerating element comprising a low-friction polymeric coating disposed on a central portion on at least one of the struts, and the coating is not disposed on portions of the strut distal to and proximal to the central portion;
such that the diameter and speed of the rotational member can be independently adjusted during removal of a blockage in the circulatory system.

14. The catheter according to claim 13, further comprising: an aspiration port along the main tubular shaft.

15. The catheter according to claim 14, wherein the aspiration port is located between a first expandable isolation member and a second expandable isolation member.

16. The catheter according to claim 15, wherein the first expandable isolation member and the second expandable isolation member are inflatable.

17. The catheter according to claim 15, wherein the first and second expandable isolation members can expand to increase their volume by at least three times.

18. The catheter according to claim 15, further comprising the first expandable isolation member and the second expandable isolation member comprise an elastic polymer.

19. The catheter according to claim 13, wherein the expandable macerating element comprises at least two struts.

20. A catheter for blockage removal for a circulatory system, comprising:
a main tubular shaft comprising a distal tip and a control handle coupled to the proximal end of the main tubular shaft;
an isolation element coupled to the main tubular shaft, the isolation element comprising a first expandable isolation member and a second expandable isolation member;
a rotational member coupled to the main tubular shaft, the rotational member comprising an expandable macerating element that includes a plurality of struts, wherein a plurality of depressions are disposed within the struts; and
an aspiration port disposed along the main tubular shaft between the first expandable isolation member and the second expandable isolation member,
wherein an abrasive component is disposed within the plurality of depressions.

21. The catheter according to claim 20, wherein the rotational member is disposed between the first expandable isolation member and the second expandable isolation member.

22. The catheter according to claim 20, wherein the first expandable isolation member and the second expandable isolation member are inflatable.

23. The catheter according to claim 20, wherein the expandable macerating element comprises at least two struts.

24. The catheter according to claim 20, wherein the first expandable isolation member and the second expandable isolation member comprise a polymer.

25. The catheter according to claim 20, wherein the rotational member can rotate at least 500 rpms.

26. The catheter according to claim 20, wherein the expandable macerating element can expand independent of rotational speed.

27. A method for removing a blockage, comprising:
inserting a catheter into a patient's circulatory system, wherein the catheter comprises a rotational member comprises a plurality of struts;
rotating the rotational member to macerate a clot such that a smooth portion of each strut interacts with a vessel wall and an abrasive portion of each strut interacts with the clot,
wherein the rotational member diameter can be expanded independent of rotational speed.

28. The method according to claim 27, further comprising: removing the catheter from the patient's circulatory system.

29. The method according to claim 27, further comprising:
expanding a first expandable isolation member and a second expandable isolation member; and
aspirating the macerated clot from between the first expandable isolation member and the second expandable isolation member.

30. The method according to claim 29, further comprising:
collapsing the first expandable isolation member and the second expandable isolation member.

31. The catheter according to claim 20, wherein a drug is disposed within the plurality of depressions.

* * * * *

UNITED STATES PATENT AND TRADEMARK OFFICE
CERTIFICATE OF CORRECTION

PATENT NO. : 10,448,969 B2
APPLICATION NO. : 15/008253
DATED : October 22, 2019
INVENTOR(S) : Sutton et al.

Page 1 of 1

It is certified that error appears in the above-identified patent and that said Letters Patent is hereby corrected as shown below:

In the Claims

Column 15, Line 11 reads, ". . . and the second expandable . . ." which should read, ". . . and a second expandable. . ."

Column 16, Line 38 & 39 reads, ". . . the catheter comprises a rotational member comprises a plurality . . ." which should read, ". . . the catheter comprises a rotational member comprising a plurality. . ."

Signed and Sealed this
Twenty-first Day of January, 2020

Andrei Iancu
*Director of the United States Patent and Trademark Office*